(12) United States Patent
Harberts et al.

(10) Patent No.: US 9,205,252 B2
(45) Date of Patent: Dec. 8, 2015

(54) MEDICAL DEVICE FOR ELECTRICAL STIMULATION

(75) Inventors: Dirk Willem Harberts, Eindhoven (NL); Rio Vetter, Ypsilanti, MI (US)

(73) Assignees: MEDTRONIC BAKKEN RESEARCH CENTER, Maastricht (NL); NEURONEXUS TECHNOLOGIES, INC., Ann Arbor, MI (US)

( * ) Notice: Subject to any disclaimer, the term of this patent is extended or adjusted under 35 U.S.C. 154(b) by 203 days.

(21) Appl. No.: 13/386,677

(22) PCT Filed: Jul. 16, 2010

(86) PCT No.: PCT/IB2010/053250
§ 371 (c)(1),
(2), (4) Date: Apr. 10, 2012

(87) PCT Pub. No.: WO2011/010257
PCT Pub. Date: Jan. 27, 2011

(65) Prior Publication Data
US 2012/0191168 A1     Jul. 26, 2012

Related U.S. Application Data

(60) Provisional application No. 61/228,231, filed on Jul. 24, 2009.

(51) Int. Cl.
*A61N 1/05* (2006.01)
*A61N 1/00* (2006.01)
(Continued)

(52) U.S. Cl.
CPC ............... *A61N 1/0534* (2013.01); *A61N 1/00* (2013.01); *A61N 1/36082* (2013.01); *A61N 2001/086* (2013.01)

(58) Field of Classification Search
CPC . A61N 2001/086; A61N 1/05; A61N 1/0488; A61N 1/086
See application file for complete search history.

(56) References Cited

U.S. PATENT DOCUMENTS 4,484,586 A * 11/1984 McMickle et al. ............. 607/122
5,330,521 A *  7/1994 Cohen .......................... 607/122
(Continued)

FOREIGN PATENT DOCUMENTS

JP     2007-521912 A    8/2007
RU       2297854 C2     4/2007
(Continued)

OTHER PUBLICATIONS

Office Action dated Oct. 1, 2013 for European Patent Application No. 10 742 283.4.
(Continued)

*Primary Examiner* — Brian T Gedeon
(74) *Attorney, Agent, or Firm* — Morgan, Lewis & Bockius LLP

(57) ABSTRACT

The present invention relates to a medical device (2) for electrical stimulation. The device comprising an implantable elongated lead system (20) having a distal end (21) and a proximal end (22), the lead system comprises one or more electrical conductors (23) for connection to one or more electrodes (24). The one or more electrical conductors are wound along a length axis (25) of the lead system with a plurality of windings, and wherein the density of windings is non-uniformly distributed along the length axis. In an embodiment, the medical device is in the form of a deep brain stimulation (DBS) device.

22 Claims, 4 Drawing Sheets

(51) Int. Cl.
*A61N 1/36* (2006.01)
*A61N 1/08* (2006.01)

(56) References Cited

U.S. PATENT DOCUMENTS

| | | | |
|---|---|---|---|
| 5,744,958 | A | 4/1998 | Werne |
| 5,797,905 | A * | 8/1998 | Fleischman et al. ............ 606/41 |
| 5,800,496 | A * | 9/1998 | Swoyer et al. ................ 607/122 |
| 6,456,888 | B1 * | 9/2002 | Skinner et al. ............... 607/116 |
| 6,477,427 | B1 * | 11/2002 | Stolz et al. ................... 607/116 |
| 8,452,416 | B2 * | 5/2013 | Djurling et al. .............. 607/116 |
| 8,731,685 | B2 * | 5/2014 | Ameri ........................... 607/116 |
| 8,983,623 | B2 * | 3/2015 | Foster et al. ................. 607/116 |
| 2005/0222656 | A1 | 10/2005 | Wahlstrand et al. |
| 2008/0129435 | A1 * | 6/2008 | Gray ............................. 336/184 |
| 2008/0243218 | A1 | 10/2008 | Bottomley et al. |
| 2008/0262584 | A1 | 10/2008 | Bottomley et al. |
| 2009/0099555 | A1 | 4/2009 | Viohl et al. |
| 2009/0149934 | A1 | 6/2009 | Ameri et al. |
| 2009/0171421 | A1 | 7/2009 | Atalar et al. |
| 2009/0254162 | A1 * | 10/2009 | Quinci et al. ................. 607/115 |
| 2011/0208280 | A1 * | 8/2011 | Li et al. ........................ 607/115 |
| 2012/0191167 | A1 * | 7/2012 | McDonald et al. ........... 607/116 |
| 2014/0031911 | A1 * | 1/2014 | Williams ...................... 607/119 |

FOREIGN PATENT DOCUMENTS

| | | |
|---|---|---|
| WO | 2008115383 A2 | 9/2008 |
| WO | 2009076169 A2 | 6/2009 |

OTHER PUBLICATIONS

Search Report and Written Opinion for International Patent Application No. PCT/IB2010/053250 dated Oct. 4, 2010.

Notice of Reason for Rejection dated Mar. 6, 2014 for Japanese Patent Application No. 2012-521134.

Second Office Action dated May 12, 2014 for Chinese Patent Application No. 201080033339.1.

Decision of Grant dated Sep. 24, 2014 for Russian Patent Application 2012106581/14(009978).

* cited by examiner

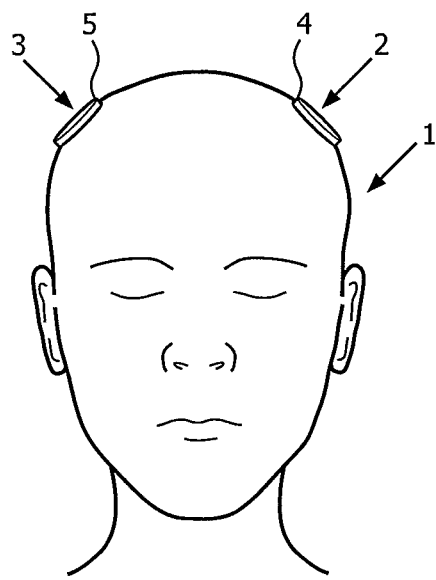
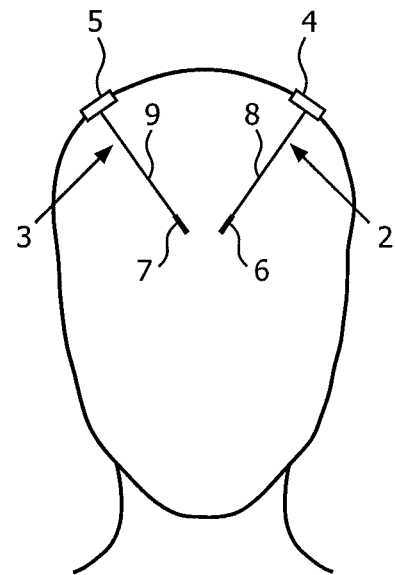
FIG. 1A    FIG. 1B
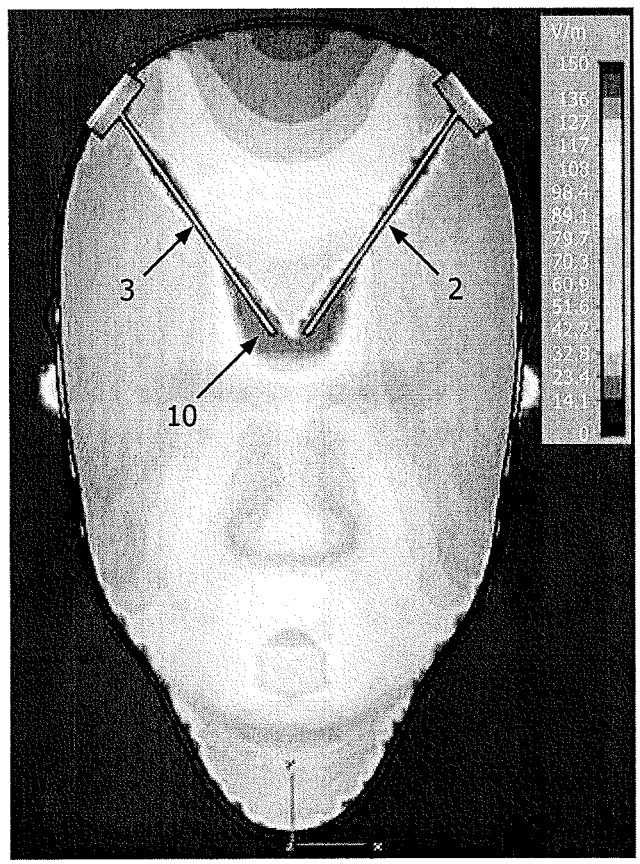
FIG. 1C

MEDICAL DEVICE FOR ELECTRICAL STIMULATION

CROSS-REFERENCE TO RELATED APPLICATIONS

This application is a National Stage Patent Application of International Patent Application No. PCT/IB2010/053250 filed on Jul. 16, 2010, which claims priority to United States Provisional Patent Application 61/228,231 filed on Jul. 24, 2009, both of which are incorporated herein by reference in their entirety.

FIELD OF THE INVENTION

The present invention relates to a medical device for electrical stimulation. In particular the invention relates to such a device comprising implantable parts.

BACKGROUND OF THE INVENTION

Electrical stimulation therapy is a fast-growing field, largely related to the successful use of implantable electrical stimulation devices for a wide range of applications. One important application is Deep Brain Stimulation (DBS). The DBS system may comprise two components: an implanted pulse generator (IPG) and a probe. The IPG is a battery powered neurostimulator that sends electrical pulses to the brain to interfere with neural activity at a target site. The probe typically consists of about 10-15 cm long wires and a plurality of electrodes. The wires connect the IPG to the electrodes, which are located at the distal end of the probe. The IPG may be calibrated by a neurologist, nurse or trained technician to optimize symptom suppression and control side effects.

Generally, however, there is a concern with implantable electrically conducting structures. It is desirable to be able to conduct Magnetic Resonance Imaging (MRI) on individuals having an implanted device. But due to the large changing magnetic fields associated with MRI, strong electrical fields can result and the associated current flow may heat up the tissue surrounding the conductor, which can damage the tissue. The problem is particularly found at conductor ends. For example, it has been shown that for an insulated 20 cm straight wire in brain tissue, the temperature may rise up to 48° C. in the normal operation mode of a 1.5 T MR systems. A temperature rise of less than 1° C. is considered safe.

The induced current densities in the electrodes and thus the undesired heating can be reduced by using electrodes with high impedances. The application of high impedance is however in conflict with having a long battery lifetime insofar the high impedance is realized as a high DC-resistance.

The published US patent application no. 2008/243218 discloses implantable leads with one or multiple conductors which from the configuration of the conductor(s) can reduce unwanted coupling to electrical field induced from the MR scanning. It is disclosed to configure the leads so they include at least one conductor with opposing proximal and distal portions, where the conductor turns back on it-self at least twice. The backward routing of the conductor, however, increases the length of the conductor.

The inventors of the present invention has appreciated that there is still a need in the art for improved implantable devices, and have in consequence devised the present invention.

SUMMARY OF THE INVENTION

It would be advantageous to achieve an implantable device which is compatible with MRI. To this end, it would be advantageous to achieve an implantable device comprising conductive parts, which minimizes or which renders low any associated temperature rises in the conductive parts during exposure to rapidly changing electromagnetic fields. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a medical device for electrical stimulation is presented that comprises an implantable elongated lead system having a distal end and a proximal end, the lead system comprises one or more electrical conductors for connection to one or more electrodes, wherein the one or more electrical conductors are wound along a length axis of the lead system with a plurality of windings, and wherein the density of windings is non-uniformly distributed along the length axis.

By winding the one or more electrical conductors, generally the impedance of the probes can be increased at high frequencies (MRI frequencies) due to self-inductance from the windings while the DC resistance at low frequencies (stimulation frequencies) can be kept sufficiently low to ensure long battery life of an associated battery-powered pulse generator. MRI frequencies are typically between 42 MHz for 1-Tesla systems to 128 MHz for 3-Tesla systems; and typically neurostimulation-stimulation pulses contain frequencies in the range from 0.001 to 10 kHz. The inventors of the present invention have realized that quite a large number of windings may be needed in order to suppress sufficiently the impedance at MRI frequencies. Thus the length of the electrical connectors needed in connection with wound conductors can be quite large. The electrical connectors may be fabricated in different ways. In one way, the electrical connectors are fabricated using thin-film technologies. Long wound structures may be difficult to make using thin-film technology. Moreover, as the length of the wires increases also the DC resistance increases which is undesirable in connection with battery life requirements. The inventors of the present invention have further realized that heating resulting from MRI scanning with an implanted medical device is non-uniformly distributed along the device. Thus by configuring the windings of the electrical conductors, such that the density of windings is non-uniformly distributed along the length axis, a high density of windings can be used in areas where this is needed, whereas a lower density of windings can be used in areas where problems related to heating are less severe. Since the same high density of windings is not used along the entire wound areas, the number of windings and thus the length of the electrical conductors are reduced, and at the same time, from the presence of the windings, the impedance can be increased sufficiently at appropriate areas to render the device suitable for use in connection with implantation and MRI.

In particular, the device may be beneficially applied in connection with deep brain simulation (DBS), since brain tissue is particularly sensitive to local heating, and moreover any damage of the brain tissue can have very severe consequences. In general, however, the device in accordance with embodiments may be applied in connection with a probe used for electrical stimulation of a number of body parts. For example, the device may be used in connection with, but not limited to, such applications as: neurostimulation, functional stimulation, spinal cord stimulation, brain stimulation, cortical stimulation, muscle stimulation, gasto-intestinal stimulation, muscle stimulation, pacing and cardiac defibrillation. For brain applications the device may be in the form of a probe extending from the skull into the brain to the target volume. For cardiac applications, the device may be in the form of a catheter that is entered in a vessel, e.g. in the groin, and extends through the vessel to the desired position in the heart.

Problems related to heating of tissue may be larger at the tip, or distal end, of the lead system than at the central and/or proximal end of the lead system. In an advantageous embodiment, the density of winding is configured so that it is higher at the distal end than at the proximal end.

It is an advantage of embodiments of the present invention that different specific configurations of the windings can be used to provide various devices which can be tailored to specific situations of use. Example embodiments comprise that the one or more electrical conductors are wound along substantially the entire length of the conductor and that the one or more electrical conductors are wound in one or more discrete sections separated by non-wound sections.

Advantageously as low as 100 windings may be non-uniformly distributed along the length of the lead system. However in embodiments, more windings may be used/needed, such as more than 125, 150, 200 or even 250 windings. These numbers are found for a study using a 10 cm long probe with a diameter of 1 mm, however it is expected that similar numbers apply for a probe of comparable size, such as for a probe with a length between 5 and 20 cm long with a diameter between 0.5 mm and 2 mm. Importantly, fewer windings are generally needed than for a similar probe having uniformly distributed windings, irrespective of the length of the probe.

In embodiments, the windings are distributed in groups having a uniform density of winding, with the group density varying along the length axis. In an alternative embodiment, the density of winding may vary continuously along the length axis with a variable length of each winding.

In embodiments, the one or more electrical conductors are wound in two or more sections, wherein at least two or the two or more sections comprises windings having opposite directions of rotation. By changing the direction of rotation at least once, the configuration is rendered less sensitive to alternating magnetic field components.

In embodiments, the medical device comprises a plurality of electrical conductors. Advantageously the plurality of electrical conductors is co-wound as tracks running in parallel along the length axis on a foil. Such a configuration may advantageously be provided using thin film technology. In an alternative embodiment, the electrical conductors are bundled together in a compound wire.

In an advantageous embodiment, the device may further comprise a power source electrically coupled to the electrical conductors at the proximal end, where the power source can be operated to generate electrical pulses at selected electrodes of the one or more electrodes. The power source may be operatively controlled by a controller, such as an IC, possibly co-located with the power source in a common housing. The controller may comprise a user interface for setting the operation of the medical device or comprise an interface for connection to a separate computer system for setting the operation of the medical device. In an embodiment, the power source (and possibly controller) is positioned in close proximity to the electrodes, e.g. as implantable or partly implantable devices in the skull (or other body part). In another embodiment, the power source (and possibly controller) may be connected via extension leads to a given position, such as to an implantable device in the breast.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1 schematically illustrates DBS devices positioned in the head of a person.

DESCRIPTION OF EMBODIMENTS

Figure 2:
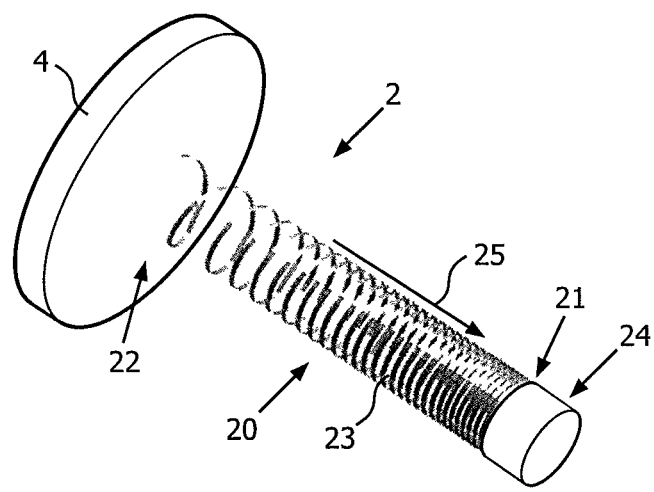
FIG. 2 schematically illustrates a medical device in the form of a DBS probe.

In this section, the present invention is primarily disclosed in connection with a medical device for electrical stimulation in the form of a device for deep brain stimulation (DBS). While, the DBS-device is an important application of the device in accordance with embodiments of the present invention, the device may be applied in connection with a large number of applications where a metal wire is used for electrical stimulation or sensing of a body part.

FIGS. 1A and 1B schematically illustrate DBS devices (also referred to as DBS probes) positioned in the head of a person. FIG. 1A schematically illustrates a person 1 having two DBS probes 2, 3 partly implanted in the head for stimulation of the left and the right side of the brain, whereas FIG. 1B illustrates a schematic cross-sectional view of the person shown on FIG. 1A. The placement and number of the DBS probes(s) is determined in accordance with the type of symptoms to be addressed. The shown example is merely for illustrative purposes as an example of a specific placement. The DBS device comprises three main components: the controller, the electrical conductors and the electrodes. The controller comprises a power source and control electronics, and it is typically referred to as the implanted pulse generator (IPG) 4, 5. The IPG is battery-powered. The IPG is typically encased in e.g. titanium housing. The IPG is connected to electrodes 6, 7 which are in contact with the brain tissue via electrical conductors (or interconnects) 8, 9. The IPG generates electrical pulses that are delivered to the brain by the electrodes 6, 7. The DBS device may comprise a large number of electrodes. For example 64 electrodes may be used. The electrodes may be individually addressable or addressable in groups. Typically a subset of electrodes is activated during therapy to direct the electrical pulses to the target site. In the Figure it is illustrated that the IPG is implanted or partly implanted in the skull. While this is an advantageous embodiment, the invention is not limited to this configuration. For example, the IPG may be implanted in the human chest and via extension leads connected to the probes 2, 3.

FIG. 1C illustrates a screen dump showing simulated field strengths occurring in the head of a person with implanted DBS probes during MRI. The Figure illustrates the two probes 2, 3 as well as the field strengths in grey scale. The scale is clipped at 150 V/m. The purpose of this illustration is to underline the fact that since equipotential lines follows the contour of the conductive probe in an external field, high field strengths result near the tip (distal end) of the probe as is pointed to by reference numeral 10. In a weakly conductive medium, such as the human brain, this leads to high current densities there because the current density is proportional to the electric field according to Ohm's law. At the tip region 10, the current densities in the brain tissue is the largest. The local temperature increase is proportional to the local power dissipation and thus to the square of the local field strength. Because the resistance of the tissue is much higher than that of the wire and the current density just outside the wire is similar to that in the wire, the local heating in the tissue will be much higher. The closer to the tip, the higher the current density and therefore the higher the heating.

FIG. 2 schematically illustrates a medical device in accordance with embodiments of the present invention, the device being in the form of a DBS probe 2. The DBS device comprises an implantable elongated lead system 20. The lead system has a distal end 21 and a proximal end 22. The lead system comprises one or more electrical conductors 23 for connection to one or more electrodes 24. The electrodes are shown schematically as a single tube however as is known to the skilled person, a given number of electrodes may be distributed and placed for contact to the brain tissues at the distal end of the lead system in a variety of configurations. The tube is merely shown for illustrative purposes. The probe comprises an IPG 4 to generate electrical pulses at selected electrodes of the one or more electrodes. An important aspect of the present invention is that the one or more electrical conductors 23 are wound along a length axis 25 of the lead system with a plurality of windings, to provide the electrical conductors with an overall helical or spiral form. The distribution of the winding is such that the density of windings is non-uniformly distributed along the length axis. Additionally the lead system may comprise a holder structure, such as a tubular structure for carrying or supporting the conductors and the electrodes. The holder structure is not shown on the Figure.

Figure 3:
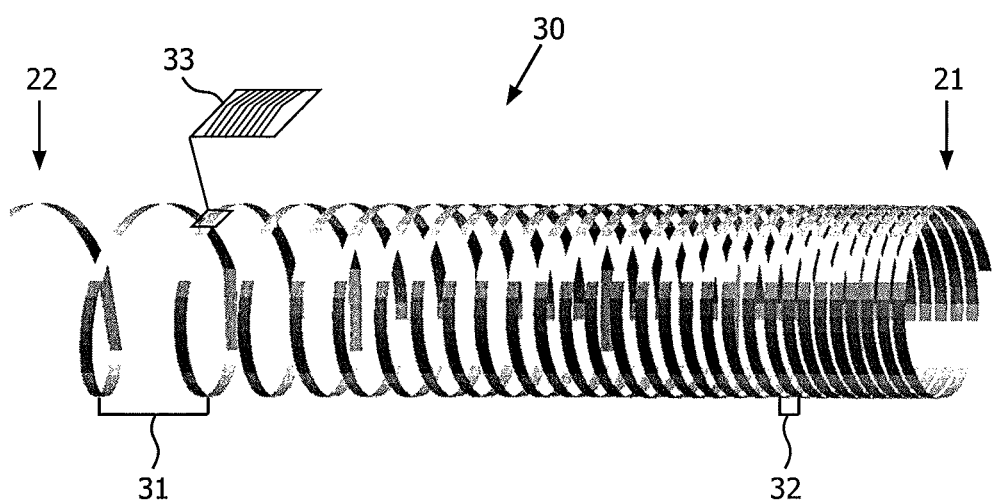
FIGS. 3 and 4 schematically illustrates embodiments of electrical conductor structures.

FIG. 3 schematically illustrates an embodiment of the electrical conductor structure 30 with a proximal end 22 and a distal end 21. In the illustrated embodiment, only a single spiraling band is shown. In embodiments, the lead system comprises a plurality of electrical conductors (and associated electrodes). In embodiments, the electrical conductors are co-wound. The co-winding may be embodied in at least two ways. In a first type of co-winding, the electrical conductors are formed as a foil with the conductors running as tracks in parallel along the length axis, this is schematically illustrated by the blow-up 33 schematically illustrating the parallel tracks. In a second type of co-winding, the electrical conductors are formed as single insulated wires which are bundled together in a compound wire, where each individual wire are configured in accordance with embodiments of the present invention. The general illustration of FIG. 3 encompasses both these situations, with the appropriate adaptation of the one or more conductors.

In a general embodiment, the density of windings is higher at the distal end than at the proximal end. In FIG. 3 the density of winding vary continuously along the length axis 25 with a variable length of each winding. Thus, the length of a winding, as represented by the spacing 31, 32 between adjacent section of two windings, is generally larger towards the proximal end 22, and generally becomes smaller towards the distal end 21.

FIG. 4 illustrates schematic embodiments of conducting structures. In FIGS. 2 and 3 the one or more electrical conductors are wound along substantially the entire length of the conductor. However as schematically illustrated in FIG. 4A, the conductor structure may comprise wound sections 40 and non-wound sections 41, 42, so that in embodiments, the windings may be provided only along a section of the conductor system. Here it is illustrated as a conductor system having windings along a central part 40 displaced towards the distal end, whereas a proximal part 41 and the distal end itself 42 may comprise non-wound sections. However, in other embodiment, generally a section of the conductor structure comprises windings, the positioning of the section may be placed in accordance with design considerations or other considerations, such that only a single non-wound section may be present. It is to be understood, that for the wound section, the density of windings is non-uniformly distributed along the length axis.

Figure 4A:
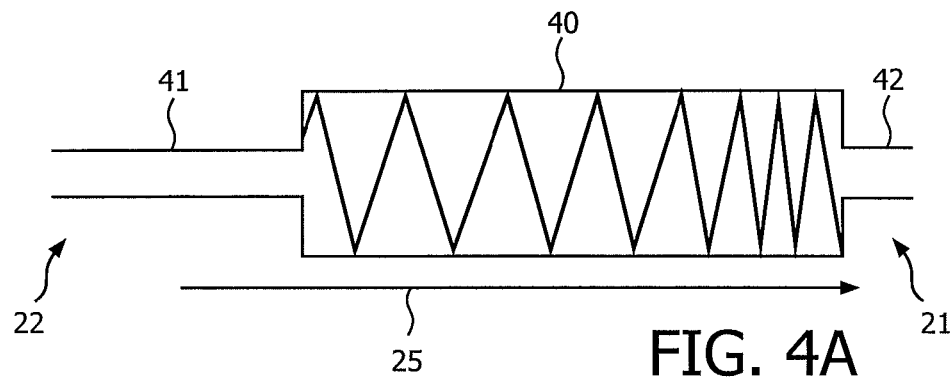
Figure 4B:
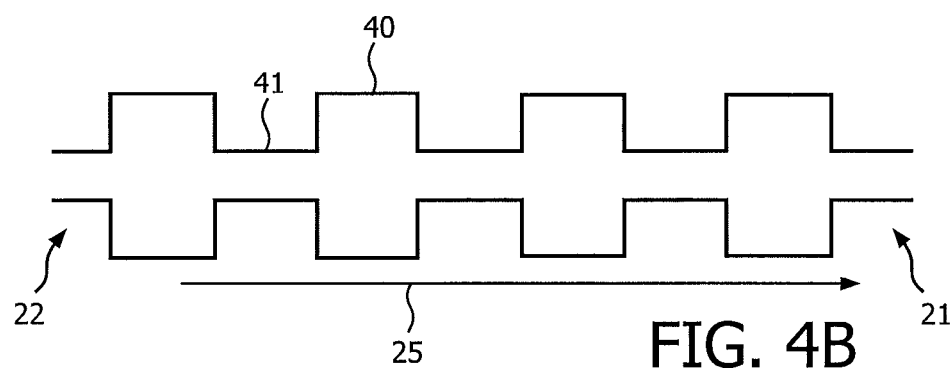

FIG. 4B schematically illustrates an embodiment, where the one or more electrical conductors are wound in a number of discrete wound sections 40 separated by non-wound sections 41. Assigning the proximal end 22 on the left and the distal end 21 on the right, it is to be understood that for the wound sections, the density of windings is non-uniformly distributed along the length axis. In an embodiment, the density of winding is so that the winding density is generally higher at the distal end than at the proximal end. In the Figure, both the wound sections 40 and the non-wound sections 41 are of equal sizes. In general, however the individual sizes of both the wound and the non-wound sections may vary.

Figure 4C:
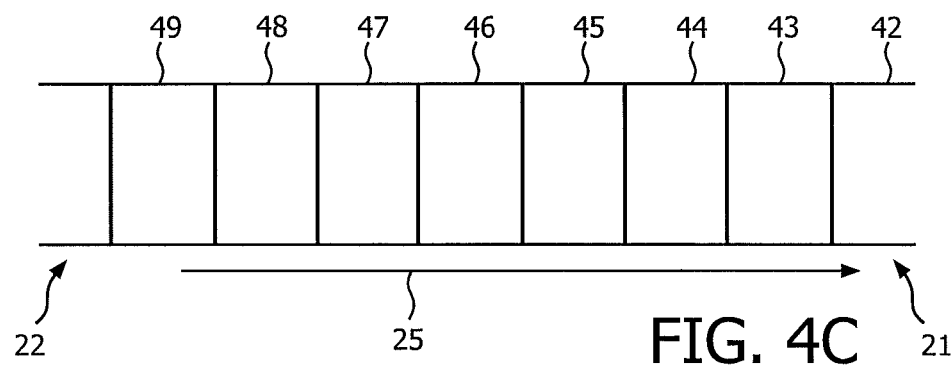

FIG. 4C schematically illustrates an embodiment, where the windings are grouped in a number of groups 42-49, wherein the density of windings within the group, that is the group density, is constant. But, the group density varies along the length axis 25, so that the group density is higher at the distal end 21 than at the proximal end 22. Thus the group density is largest in group 42, less in group 43, and so forth, until group 49 where it is smallest.

Figure 4D:
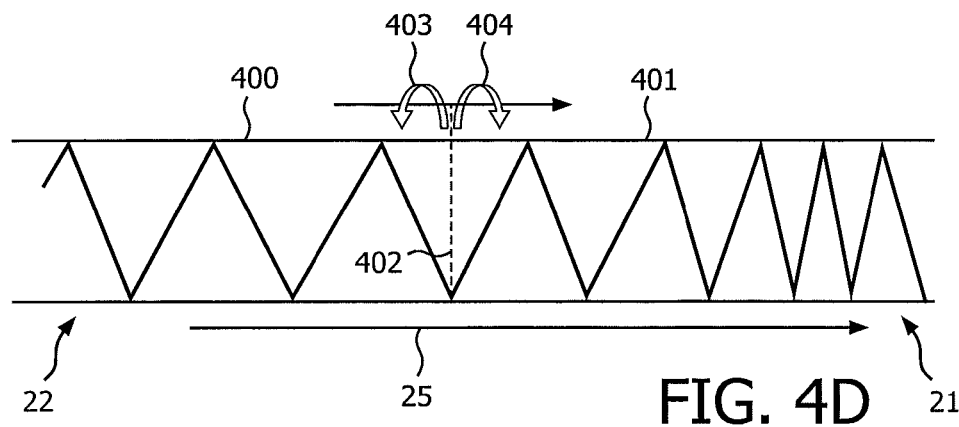

FIG. 4D schematically illustrates an embodiment, where two sections 400, 401 comprise windings having opposite directions of rotation. In the embodiment, it is illustrated that at a given position 402, the direction of the windings changes from a first direction 403 to a second opposite direction 404. In the Figure it is indicated that the direction of rotation is changed halfway, however, this is not necessarily the case. Moreover, the direction of rotation may be changed two or more times along the length axis 25.

The specific features of the conducting structure as disclosed in connection with the FIGS. 3 and 4A to 4D may be combined in any way within the scope of the present invention.

FIG. 5 shows simulations of different conductor configurations. The calculations are simulations of electric field strengths arising in brain tissue during MRI due to the present of an implanted conductor. In order to achieve accurate simulation results at acceptable simulation times, the following model is considered. The DBS device is considered in a homogeneous block of material with the electrical properties representative of the human brain. An external plane wave was incident on this block of material such that without any metal wire, the electric field strength in the center was about 900 V/m. The presence of the wire results in a strong increase in the electric field strength. In the Figure the scale has been clipped to 2000 V/m. The change in contours of the clipped values gives a clear indication of the strong reduction in field strength due to the winding of the wire. The simulations are performed using the 3D electromagnetic simulation program MicroWave Studio from CST (www.cst.com). The controller box is modeled as a solid cylinder with a height of 7 mm and a diameter of 24 mm. The lead system is modeled as a thin cylinder of 10 cm length and diameter of 1.6 mm. The interface of the electronics is modeled by a 50Ω resistor between the wire and the solid box. It is noted that the parallel conductors in a probe are routed very close to each other and are therefore strongly coupled at MRI frequencies. This coupling is so strong that the parallel conductors can be modeled as one single wire.

Figures 5A, 5B, 5C, 5D, 5E, 5F:
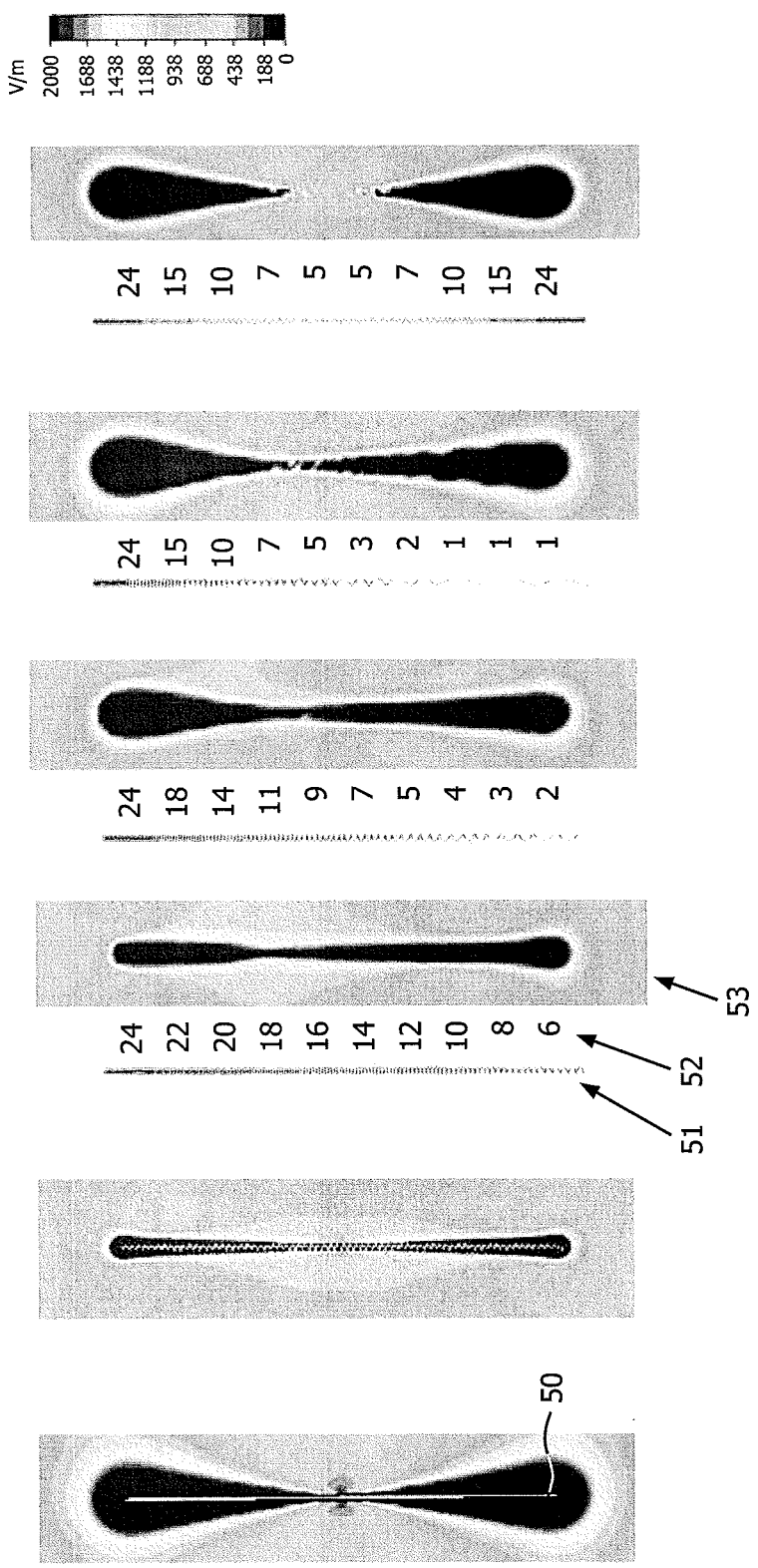
FIG. 5 shows example calculations of different conductor configurations.

FIG. 5A illustrates the simulation result for a 10 cm long straight wire and FIG. 5B illustrates the simulation result for a conducting structure comprising 250 uniformly distributed windings along the length axis of the conducting structure. FIGS. 5A and 5B are shown for comparison to FIGS. 5C to 5F which show simulation carried out for a DBS with a non-uniform number of windings distributed along the length axis of the conducting structure in accordance with embodiments of the present invention, and in particular in connection with an embodiment as schematically illustrated in FIG. 4C. All the Figures comprise the DBS probe centrally placed. This is most easily seen in FIG. 5A as indicated by reference numeral 50, however also the other Figures comprise the probe even though it is less visible due to the color scale.

FIG. 5A shows a simulation result obtained for a 10 cm long straight wire with a diameter of 1 mm. It shows that quite a large area has a field strength about 2000 V/m. From detailed inspection of the distribution, it can be assessed that this field strength and distribution is unacceptable in relation to MRI since it will lead to too high temperature rises in the brain tissue.

FIG. 5B shows a simulation result obtained for a 10 cm long wire with a diameter of 1 mm having 250 uniformly distributed windings along the probe. From inspections of simulations performed for probes with uniformly distributed windings, it has been assessed that 250 windings are appropriate for use, even though this is not a hard limit.

FIGS. 5C to 5F show a simulation result obtained for a 10 cm long wire with a diameter of 1 mm having non-uniformly distributed windings. Each of the probes is sectioned into groups of one centimeter with a constant density of windings within the group, also referred to as the group density. Each of the Figures shows three entities. At the left is shown a schematic illustration of the specific probe 51. In the middle is shown the group density along the probe. Thus for the probe in FIG. 5C, the distal end comprises 24 windings/cm, the next group comprises 22 windings/cm and so forth until the proximal end which comprises 6 windings/cm. At the right is shown the simulation result 53 for the specific probe configuration. From inspection of the simulations performed for probes with non-uniformly distributed windings, it has been assessed that the probe in FIG. 5C is appropriate for use in connection with MRI. However, other specific distributions of densities of windings can be used as well. It is within the capabilities of the skilled person to assess appropriate specific winding configurations. Specifically for the configuration of FIG. 5C, only 150 windings is used, which is a reduction of 60% as compared to the configuration of FIG. 5B having 250 uniformly distributed windings.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical device for electrical stimulation, the device comprising:
   an implantable elongated lead system having a distal end and a proximal end, the lead system comprises one or more electrical conductors for connection to one or more electrodes,
   wherein the one or more electrical conductors are wound along a length axis of the lead system with a plurality of windings that extend to the distal end, and
   wherein spacing between any adjacent two of the plurality of windings is larger than spacing between any other more distal adjacent two of the plurality of windings.

2. The device according to claim 1, wherein the one or more electrical conductors are wound along substantially an entire length of the lead system.

3. The device according to claim 1, wherein the number of the plurality of windings is larger than 100 distributed along the length axis of the lead system.

4. The device according to claim 1, wherein the one or more electrical conductors are wound in two or more sections, wherein at least two or more sections comprises windings having opposite directions of rotation.

5. The device according to claim 1, wherein the density of the plurality of windings varies continuously along the length axis with a variable length of each of the plurality of windings.

6. The device of claim 1, wherein the one or more electrical conductors comprises a plurality of electrical conductors, wherein the plurality of electrical conductors are co-wound.

7. The device according to claim 6, wherein the plurality of electrical conductors are formed as a foil with the plurality of electrical conductors running in parallel along the length axis.

8. The device according to claim 6, wherein the plurality of electrical conductors are bundled together in a compound wire.

9. The device according to claim 1, further comprising a power source electrically coupled to the one or more electrical conductors at the proximal end, where the power source can be operated to generate electrical pulses at selected electrodes of the one or more electrodes.

10. The device according to claim 1, wherein the application of the device is selected from the group consisting of: neurostimulation, functional stimulation, spinal cord stimulation, brain stimulation, cortical stimulation, muscle stimulation, gasto-intestinal stimulation, muscle stimulation, pacing and cardiac defibrillation.

11. The device according to claim 1, suitable for deep brain stimulation, wherein the device comprises a power source that can be operated to generate electrical pulses suitable for electrical stimulation of the brain.

12. A medical device for electrical stimulation, the device comprising:
   an implantable elongated lead system having a distal end and a proximal end, the lead system including a plurality of electrical conductors for connection to one or more electrodes, wherein the plurality of electrical conductors are co-wound along a length of axis of the lead system with a plurality of windings that extend to the distal end, and wherein spacing between any adjacent two of the plurality of windings is larger than spacing between any other more distal adjacent two of the plurality of windings, wherein the plurality of electrical conductors form a single spiraling band.

13. The device according to claim 12, wherein the plurality of electrical conductors are wound along substantially an entire length of the lead system.

14. The device according to claim 12, wherein a number of the plurality of windings is larger than 100 distributed along the length axis of the lead system.

15. The device according to claim 12, wherein the plurality of electrical conductors are wound in two or more sections, wherein at least two of the two or more sections comprises windings having opposite directions of rotation.

16. The device according to claim 12, wherein a density of the plurality of windings varies continuously along the length axis with a variable length of each of the plurality of windings.

17. The device according to claim 12, wherein the plurality of electrical conductors are formed as a foil with the plurality of electrical conductors running in parallel along the length axis.

18. The device according to claim 12, wherein the plurality of electrical conductors are bundled together in a compound wire.

19. The device according to claim 12, further comprising a power source electrically coupled to the plurality of electrical conductors at the proximal end, where the power source can be operated to generate electrical pulses at selected electrodes of the one or more electrodes.

20. The device according to claim 12, wherein application of the device is selected from the group consisting of: neuro-stimulation, functional stimulation, spinal cord stimulation, brain stimulation, cortical stimulation, muscle stimulation, gasto-intestinal stimulation, muscle stimulation, pacing and cardiac defibrillation.

21. The device according to claim 12, suitable for deep brain stimulation, wherein the device comprises a power source that can be operated to generate electrical pulses suitable for electrical stimulation of the brain.

22. A medical system, comprising:

an implantable pulse generator; and a lead coupled o the implantable pulse generator, the lead comprising at least one electrical conductor having a plurality of windings that extend from a proximal end to a distal end of the lead along an entire length axis of the lead, wherein spacing between any adjacent two of the plurality of windings is larger than spacing between any other more distal adjacent two of the plurality of windings.

* * * * *